(12) United States Patent
Fidrich et al.

(10) Patent No.: US 7,864,994 B2
(45) Date of Patent: Jan. 4, 2011

(54) SYSTEMS, METHODS AND APPARATUS OF HANDLING STRUCTURES IN THREE-DIMENSIONAL IMAGES HAVING MULTIPLE MODALITIES AND MULTIPLE PHASES

(75) Inventors: Márta Fidrich, Szeged (HU); Judit Bak-Kanyó, Dömsöd (HU); Lehel M. Ferenczi, Budapest (HU); Attila Ferik, Kerepes (HU)

(73) Assignee: General Electric Company, Schenectady, NY (US)

( * ) Notice: Subject to any disclaimer, the term of this patent is extended or adjusted under 35 U.S.C. 154(b) by 1364 days.

(21) Appl. No.: 11/352,477

(22) Filed: Feb. 11, 2006

(65) Prior Publication Data

US 2007/0189589 A1   Aug. 16, 2007

(51) Int. Cl.
*G06K 9/00* (2006.01)
(52) U.S. Cl. ....................... 382/128; 382/132

(58) Field of Classification Search .................. 382/100, 382/128–132; 378/98.9, 901.92, 16, 8, 15, 378/901; 345/738, 735, 730, 732, 800, 786, 345/788, 716, 801, 156, 418, 501; 707/100, 707/104, 600
See application file for complete search history.

(56) References Cited

U.S. PATENT DOCUMENTS 6,734,880 B2 * 5/2004 Chang et al. ............... 715/738
7,106,891 B2 * 9/2006 Wyman et al. ............. 382/128
7,116,749 B2 * 10/2006 Besson ........................ 378/16

\* cited by examiner

*Primary Examiner*—Samir A. Ahmed
*Assistant Examiner*—Mehdi Rashidian
(74) *Attorney, Agent, or Firm*—Dean Small; Small Patent Law Group

(57) ABSTRACT

Systems, methods and apparatus are provided through which in some embodiments, a structure manager explicitly creates a container of graphical objects of anatomical regions by adding a structure, or the structure manager implicitly creates graphical objects of a group of anatomical regions through an organ segmentation process.

4 Claims, 12 Drawing Sheets

SYSTEMS, METHODS AND APPARATUS OF HANDLING STRUCTURES IN THREE-DIMENSIONAL IMAGES HAVING MULTIPLE MODALITIES AND MULTIPLE PHASES

RELATED APPLICATION

This application is related to copending U.S. application Ser. No. 10/858,241, filed Jun. 1, 2004 and titled "Systems and Methods for Segmenting an Organ in a Plurality of Images."

This application is related to copending U.S. application Ser. No. 10/935,893, filed Sep. 8, 2004 and titled "Contrast Agent Imaging-Driven Health Care System and Method."

This application is related to copending U.S. application Ser. No. 10/907,690, filed Apr. 12, 2005 and titled "Method and System for Automatically Segmenting Organs from Three Dimensional Computed Tomography Images."

This application is related to copending U.S. application Ser. No. 11/352,514, filed Feb. 11, 2006 and titled "SYSTEMS, METHODS AND APPARATUS OF HANDLING STRUCTURES IN THREE-DIMENSIONAL IMAGES"

FIELD OF THE INVENTION

This invention relates generally to imaging systems, and more particularly to three dimensional imaging systems.

BACKGROUND OF THE INVENTION

Images of a structure of an object are generated in one of a number of conventional modalities. In medical care, where the object is a patient, the images are suitable for diagnostic purposes or radiotherapy treatment, or for planning surgery.

Examples of the conventional modalities include conventional X-ray plane film radiography, computed tomography (CT) imaging, magnetic resonance imaging (MRI), and nuclear medicine imaging techniques, such as positron emission tomography (PET) and single photon emission computed tomography (SPECT).

A three-dimensional (3D) medical image is a collection of adjacent (transaxial) two-dimensional (2D) slices. Clinicians recombine anatomical elements of 2D slices to form a 3D image of an anatomical region or an organ. This recombination process is usually termed reconstruction.

During clinical diagnosis, the patient's internal anatomy is imaged to determine how a disease has progressed. The infected tissues show some differences from normal tissues. Also, the patient may have some type of individual differences or abnormalities regarding healthy tissues.

The clinicians identify and handle critical anatomical regions, and in particular organs, on several images for planning of treatment or surgery. Handling critical anatomical regions and organs includes tracing the outline of these regions and organs, which yields graphical objects. A graphical object visually marks for the clinician the separation of an anatomical region from the other parts of an image. Manually drawing the individual contours on a contiguous set of 2D slices then combining them is very time consuming and labor intensive. The time and labor increases significantly with the number of image slices, the number and sizes of the organs, tumors, etc. in the anatomical area of interest. The quality of the contouring and 3D visual graphical objects generated from the 2D slices depends on the resolution and contrast of the 2D images, and on the knowledge and judgment of the clinician performing the reconstruction. However, conventional methods of segmentation of anatomical regions and organs by the clinician require a considerable amount of time to be performed and subjectivity in the judgment of the clinician in manual segmentation introduces a high degree of impression.

The graphical objects also need to be managed. Conventional methods of managing the graphical objects are inefficient and overwhelming to the abstraction skills of human clinicians.

For the reasons stated above, and for other reasons stated below which will become apparent to those skilled in the art upon reading and understanding the present specification, there is a need in the art for more efficient methods and apparatus of managing graphical objects. There is also need to reduce the time and impression of human clinicians in segmenting anatomical regions.

BRIEF DESCRIPTION OF THE INVENTION

The above-mentioned shortcomings, disadvantages and problems are addressed herein, which will be understood by reading and studying the following specification.

The systems, method and apparatus described below are a complex system, yet are an efficient and user-friendly system, which manages organization of graphical objects and manual/automated contouring (segmentation). The systems, method and apparatus described below are suitable for any kind of image modality and any kind of segmentation algorithm.

In one aspect management of the graphical objects includes grouping the objects together for classification. In other aspects, the management of the graphical objects includes measuring characteristics of the graphical objects.

In a further aspect, the system to organize anatomically related parts into structures includes a workflow system that receives a plurality of images and at least one user input from an external source. The workflow system includes two modules or components. One of the two modules provides manual or an automated contouring of the anatomical regions and organs on images in accordance with the user input that ultimately yields graphical objects. The manual contouring is performed either by tracing or by follow-up techniques. The automated contouring is performed either by thresholding or by organ segmentation that has a technical effect of being considerably faster and more precise than conventional manual techniques. The other module provides organization to the graphical objects by creating explicitly or implicitly, containers or group of containers, in accordance with the user input that ultimately yields organized containers. A container of a graphical object is also known as a structure. The clinicians usually use the name of the container to identify the graphical object.

In another aspect, the system eases organization of structures by flexible usage of structures. That is, the system creates, stores, retrieves and combines anatomically relevant parts in structures.

In yet another aspect, the systems, method and apparatus described below is applicable to structure handling from explicit or implicit structure creation, via drawing graphical object contour either manually (tracing, follow up) or automatically (thresholding, organ segmentation), to structure management and usage. A segmentation workflow can be used in two different ways. The first way greatly supports user interaction, intended for organs that are difficult to segment fully automatically (e.g. because of low contrast). Another process supports batch mode, intended for organs whose segmentation is relatively long.

In still another aspect, the systems, method and apparatus described below provide easy-to-use workflow in the correct order. The systems, method and apparatus described below elevates abstraction level, provides consistent organization with clean layout, while allowing a user to maintain control during the segmentation process with a large number of choices and options.

In a further aspect, a method to organize anatomically related parts into structure groups includes creating a plurality of graphical objects of related anatomical regions and organs, and combining the plurality of structures of the graphical objects of the related anatomical regions and organs.

In yet a further aspect, a method to manage groups of structures of includes creating a plurality of graphical objects from predefined data and creating graphical objects from user-defined data.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, embodiments of methods are described. In the third section, the hardware and the operating environment in conjunction with which embodiments may be practiced are described. In the fourth section, particular implementations are described. Finally, in the fifth section, a conclusion of the detailed description is provided.

Overview

Figure 1:
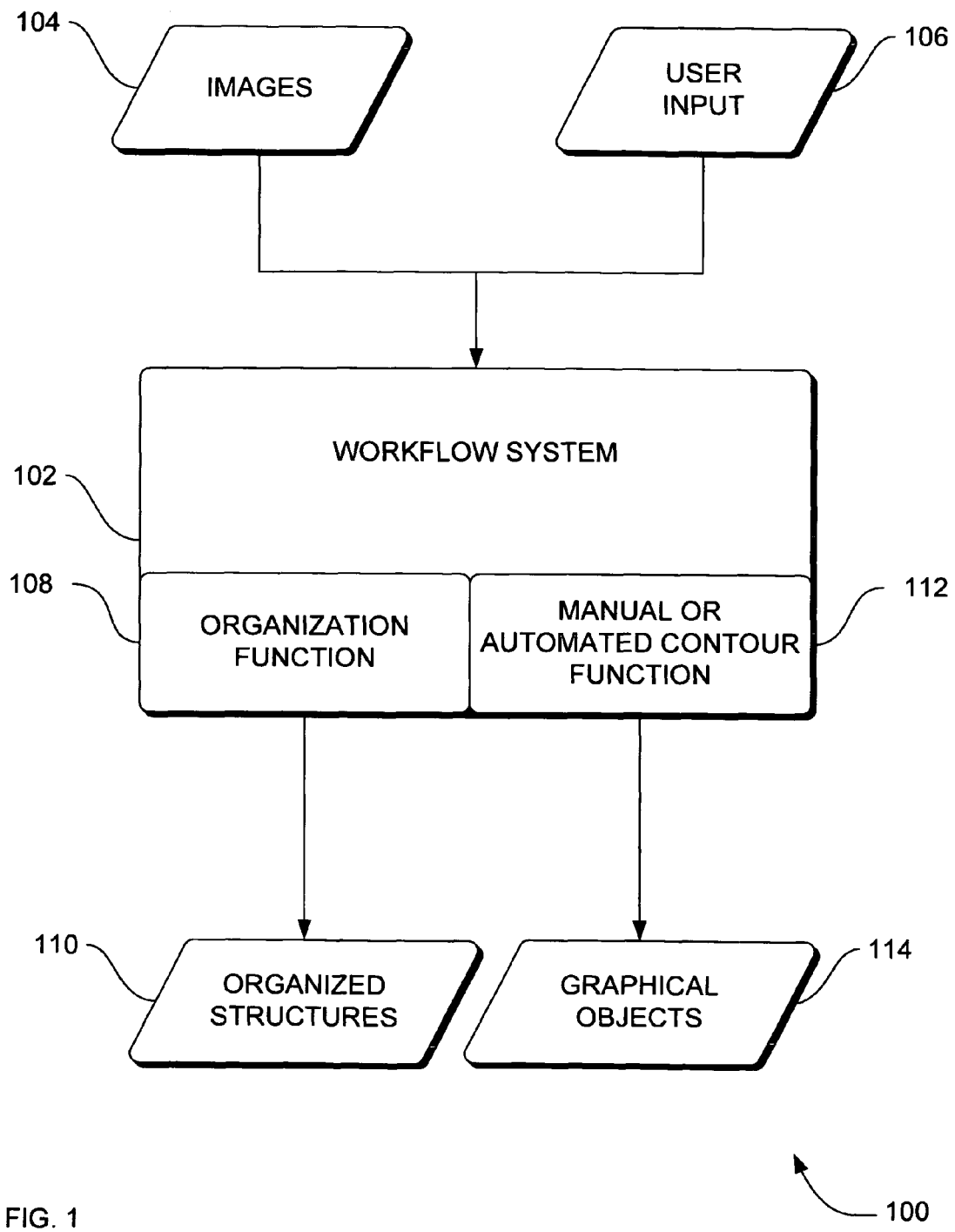
FIG. 1 is a block diagram of an overview of a system to organize anatomically related parts into structures.

FIG. 1 is a block diagram of an overview of a system to organize anatomically related parts into structures. System 100 solves the need in the art for more efficient methods and apparatus of managing graphical objects. System 100 also solves the need in the art to reduce the challenge to humans in managing graphical objects. System 100 also reduces time and improves precision of human clinicians in segmenting anatomical regions.

System 100 includes a workflow system 102 that receives a plurality of images 104 and at least one user input 106 from an external source. The workflow system 102 includes two modules or components. One of the two modules 108 provides organization to the images 104 by creating explicitly or implicitly structures or group of structures in accordance with the user input 106 that ultimately yields organized structures 110. Thus system 100 solves the need in the art for more efficient methods and apparatus of managing graphical objects and reducing the challenge to humans in managing graphical objects.

The other module 112 provides manual or an automated contouring of the images 104 in accordance with the user input 106 that ultimately yields graphical objects 114. The manual contouring is performed either by tracing or by follow-up techniques. The automated contouring is performed either by thresholding or by organ segmentation that has a technical effect of being considerably faster and more precise than conventional manual techniques. Thus system 100 also reduces time and improves precision of human clinicians in segmenting anatomical regions.

In some embodiments, the structures of system 100 and methods 200-400 are organized in a tree structure in accordance with the occurrence of anatomical regions. One embodiment of such a tree structure is shown in apparatus 600 in FIG. 6.

System 100 is suitable for any kind of image modality such as X-Ray plane film radiography, computed tomography (CT) imaging, magnetic resonance imaging (MRI), and nuclear medicine imaging techniques, such as positron emission tomography (PET) and single photon emission computed tomography (SPECT). System 100 is also suitable for any kind of segmentation algorithm.

Figure 5:
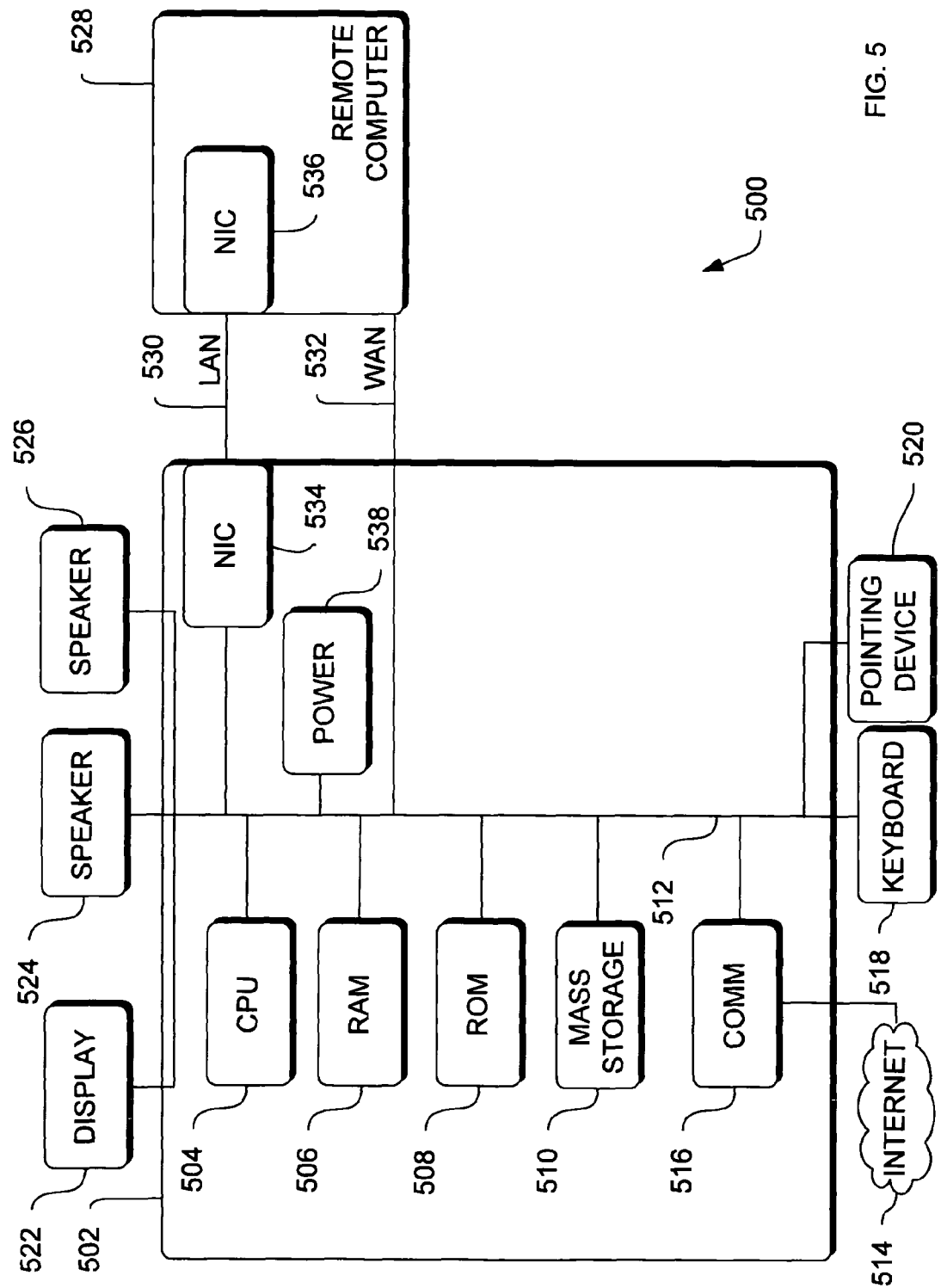
FIG. 5 is a block diagram of a hardware and operating environment in which different embodiments can be practiced.

Some embodiments operate in a multi-processing, multi-threaded operating environment on a computer, such as computer 502 in FIG. 5. While the system 100 is not limited to any particular workflow system 102, image 104, user input 106, organization function 108, organized structures 110, contour function 112 and graphical objects 114 for sake of clarity a simplified workflow system 102, image 104, user input 106, organization function 108, organized structures 110, contour function 112 and graphical objects 114 are described.

Method Embodiments

In the previous section, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 200-400 are performed by a program executing on, or performed by firmware or hardware that is a part of, a computer, such as computer 502 in FIG. 5.

Figure 2:
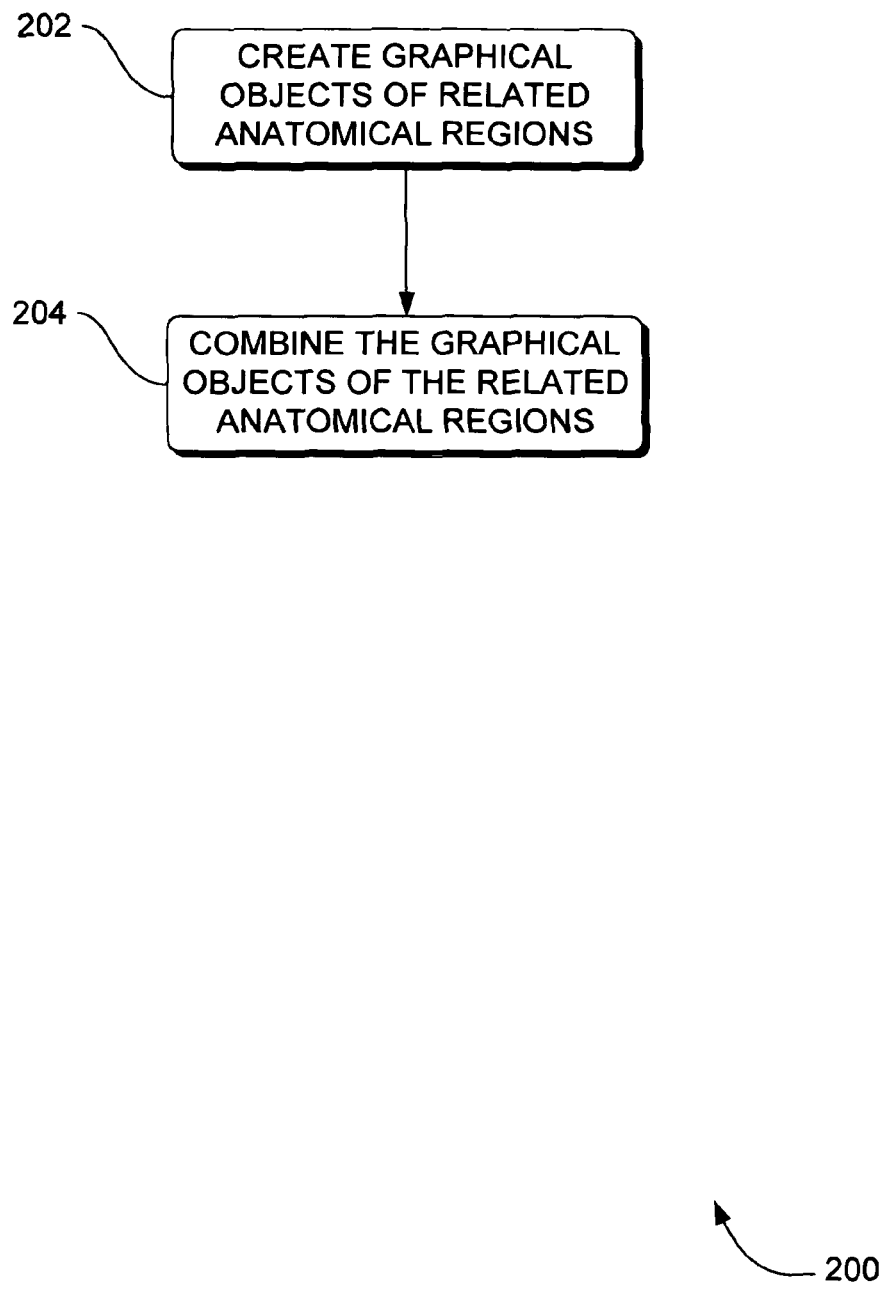
FIG. 2 is a flowchart of a method to organize anatomically related parts into structure groups according to an embodiment.

FIG. 2 is a flowchart of a method 200 to organize anatomically related parts into structure groups according to an embodiment. Method 200 solves the need in the art to reduce the challenge to humans in managing graphical objects. Method 200 also reduces time and improves precision of human clinicians in segmenting anatomical regions.

Method 200 includes creating 202 a plurality of graphical objects of related anatomical regions. Method 200 also includes combining 204 the plurality of structures of the graphical objects of the related anatomical regions.

Method 200 organizes anatomically relevant parts into structure groups, regardless whether the structure groups are explicitly or implicitly created in action 202. In some embodiments, explicit creation of a structure or a group of structures includes adding the structure to an existing or a newly created structure group. In addition a group of structures can also be added to other groups of structures.

In some embodiments, implicit creation of a structure or a group of structures is accomplished by an organ segmentation process. One example of an organ segmentation process is lung segmentation that automatically creates structures and an outline of both the right and left lungs.

In some embodiments, in implicit creation of a structure or a group of structures, the user is not required to create a structure explicitly beforehand using segmentation. A segmentation result is stored in a visual graphical object that is created in response to the segmentation, the structure container of the graphical objects being maintained by a structure handling system. Optionally, the user stores the segmentation result in an already existing structure. When a visual graphical object is created in response to the segmentation, a predefined set of properties (e.g. name, color, type) are referenced during the creation.

Segmentation algorithms may create more than one visual graphical object (e.g. lung: right lung and left lung) simultaneously. The structure container of these graphical objects is stored in a structure group that is created in response to the segmentation, and that are maintained by a structure group handling system.

Some embodiments of method 200 further include one or more of the following operations on one or more visual graphical object(s) such as multiple selection, union, join, difference, intersect, delete, margin, set visibility, set transparency and/or set color, in any combination of operations.

The organ segmentation process provides delineation of anatomical regions. Segmentation of organs is based on image features and anatomical information. To adapt to different user needs in segmentation, a workflow of segmentation can perform in two different methods. The first method is particularly well suited for organs that are difficult to fully segment without human interaction, as the result of image problems such as low image contrast. The first process supports batch mode via usage of segmentation protocols, which is particularly well-suited for organs whose segmentation is relatively long. Batch mode means processing in the background, that is, interaction from the user is not required.

One general method of segmentation workflow includes, selecting an organ to be segmented (in batch mode, several organs can be selected and collected into a segmentation protocol); an optional action of defining seed points or curves; an optional action of adding seed(s) (some segmentation algorithms may run without providing any seed, especially within a protocol); accepting user interaction during segmentation, the level of interaction depending upon the execution mode of either interactive segmentation or batch mode via protocols; and adding segmented object(s) to the structure (group) list.

In some embodiments, several types of seeds are provided to start the automatic segmentation, such as: no seed at all, seed point, curve, segment or region of interest (ROI). Providing the seed can be performed in various ways, such as typing point coordinates, clicking and drawing by the user. In addition, suitable seed(s) may be presented to the user, and then user decides which if any seed to accept as given, or adjusting the presented seed(s), or the user can provide different one(s).

In some embodiments, selecting segmentation parameters has also numerous alternatives, such as: direct typing, loading previously chosen and saved parameter set, or selection among options. The segmentation parameters minimize the amount of interaction from the user.

In some embodiments, visual cues are provided to help guide the user in data entry. Examples of the visual cues include drawing a circle around the graphical cursor while user aims to select a seed point for eye ball segmentation, interactively showing the initial region of segmentation, which can range from a minimal region in case of a simple region growing algorithm to a roughly-fit model in case of model-based segmentation, and a warning that a seed is not correct (e.g. user accidentally clicked in image background. User has the possibility to modify seed points and curves prior starting the segmentation algorithm. This includes re-typing coordinates, clicking a new seed point, re-placing the point by dragging, redrawing completely a curve, editing a curve or re-placing the curve by dragging, etc.

In some embodiments, cases of new seed selection or existing seed modification are distinguished. A cue used in distinguishing between cases of new seed selection or existing seed modification is whether graphical cursor location is near to an existing seed or not, e.g. whether the user has already clicked 1 seed point and the algorithm needs 2 seed points. When the user clicks in the vicinity of the existing point again the system interprets the click as a modification action, otherwise the clicking is interpreted as a creation action. The size of the vicinity is set to a predetermined default value, but the user can also define the size of the vicinity an override the default value.

In some embodiments, interactive segmentation provides flexibility and control while maintaining efficiency and ease of use to the user. In interactive segmentation, a progress bar displays advancement of the segmentation process in time. In addition, a "cancel" will cancel the interactive segmentation when clicked by the user. When the interactive segmentation is cancelled, the temporary result becomes the finale result, which is helpful to an impatient user who is willing to accept the current state of the precision of interactive segmentation. The user is able to continue the operation after a segmentation process is cancelled, with the same or different set of segmentation parameters. The balance between precision and speed can be also adjusted as a user preference.

In some embodiments, a segmentation process can be paused or broken, and thereafter continued, which allows a user to a review the temporary result, interactively correct the results between a break and continue operation. The interactive correction can be organ-specific (extension of the ongoing segmentation algorithm) or general modification with manual editing tools. The actions of interactive editing can be undo and redo, which can be performed step by step, or the user can select a state or action from the undo/redo list.

In some embodiments of batch segmentation, several organs are collected for one background processing.

In some embodiments, interactive segmentation protocols and batch segmentations are defined in a variety of ways. In one example, a list of all the organs that need to be automatically segmented is received from the user.

In another embodiments, the organs are ranked in an optimal execution order, so that:

1) Pre-processing of segmentation requires minimum execution time (optimization in speed): e.g. Smoothing of image data is performed only once and on the union of ROIs containing the individual organs. As a consequence, saving time is important in case of neighboring organs, such as liver—right kidney or spleen—left kidney.

2) Suitable seed(s) are located (optimization in interaction). In one example, the spinal cord is segmented either with a user-given seed point or without any seed (system is able to find a proper seed based on center position and intensity value of spine). Then rough position of other organs is automatically found with respect to position and bending of spine.

3) Leakage is minimized (optimization in quality). In one example, after segmentation of the spinal cord, organs of large size (e.g. liver) are segmented, because they have less chance to visually leak. Finally small organs or organs with complex shape (e.g. kidney) follows, during their segmentation the already segmented organs are used as constraints to prevent leakage.

A background segmentation protocol process is started after receiving an indication of start. The background segmentation protocol process is performed with the following seed options: 1) All necessary seeds for all the organs are received from the user in advance. 2) The seeds only for some "difficult" organs are received from the user in advance; for the other organs, the seeds are determined from the protocol. 3) All seeds are determined by and received from the protocol. When the seed is determined by the protocol, the user is solicited or queried for optional confirmation about seeds when segmentation of the actual organ is starting.

In some embodiments, execution of segmentation protocol conforms to the following requirements: 1) Organs are segmented in the order defined by the system. 2) The user is solicited to verify then accept/adjust/re-give seed, as requested by the user during protocol start-up. 3) Different organs are not allowed to overlap each-other, which reduces leaking between neighboring organs. 4) Displaying progress of protocol execution. In a default mode, a progress bar is display and the user is solicited as to whether temporary results of the segmentation are to be displayed. 5) The user is solicited to cancel either the actual organ segmentation only or the whole protocol. 6) The user is solicited to pause or break the segmentation, after that the temporary result of that organ will become the finale one, and the protocol continues with the segmentation of the next organ. Interactive correction and continuation (of segmentation of the organ stopped) is not supported after a break and is not supported during protocol execution.

Figure 3:
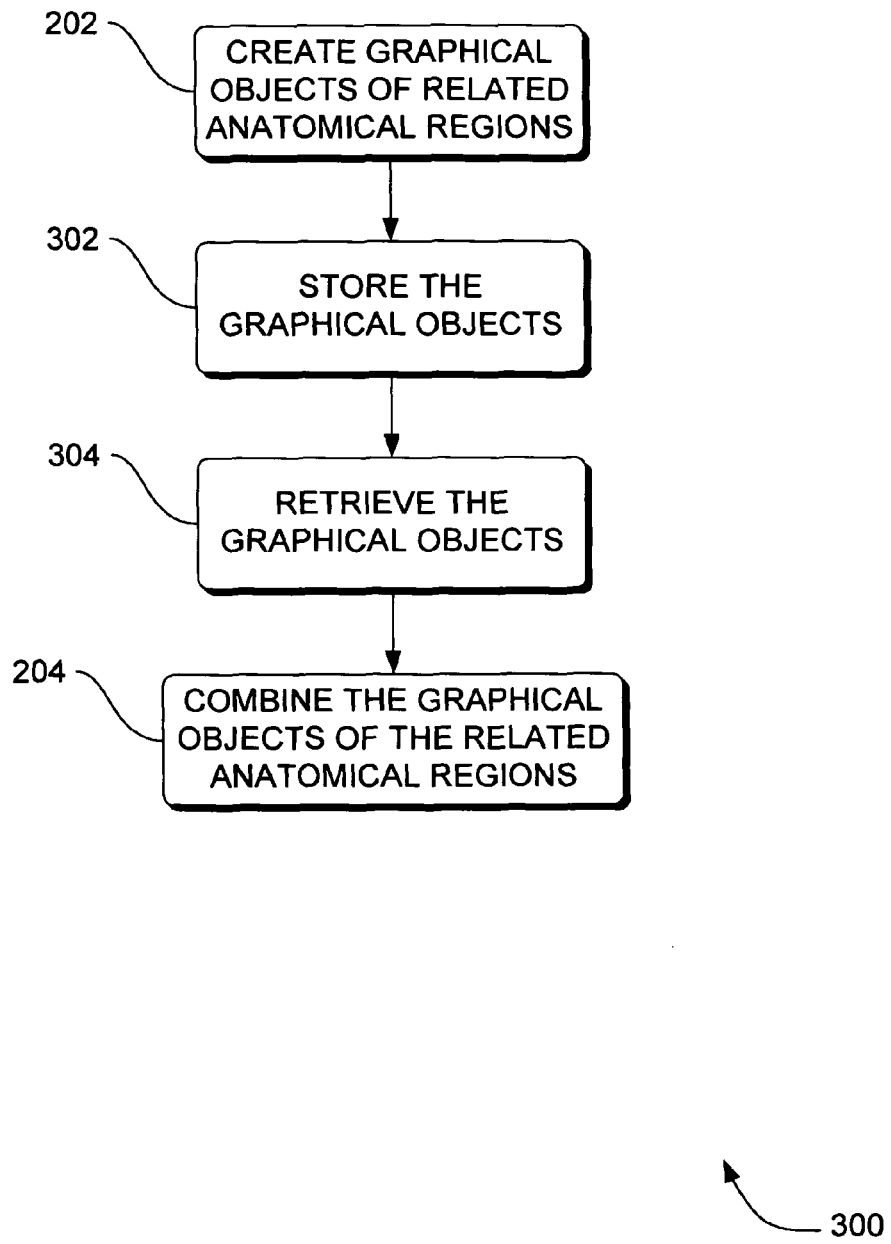
FIG. 3 is a flowchart of a method to organize anatomically related parts into structure groups according to an embodiment.

FIG. 3 is a flowchart of a method 300 to organize anatomically related parts into structure groups according to an embodiment. Method 300 solves the need in the art to reduce the challenge to humans in managing visual graphical objects. Method 300 also reduces time and improves precision of human clinicians in segmenting anatomical regions.

Method 300 includes creating 202 a plurality of graphical objects of related anatomical regions and storing 302 the graphical objects to a computer-accessible media, such as a random-access memory (RAM), a read-only memory (ROM), and/or one or more mass storage devices.

Method 300 also includes retrieving 304 the graphical objects from the computer-accessible media and combining 204 the retrieved graphical objects of the related anatomical regions.

Figure 4:
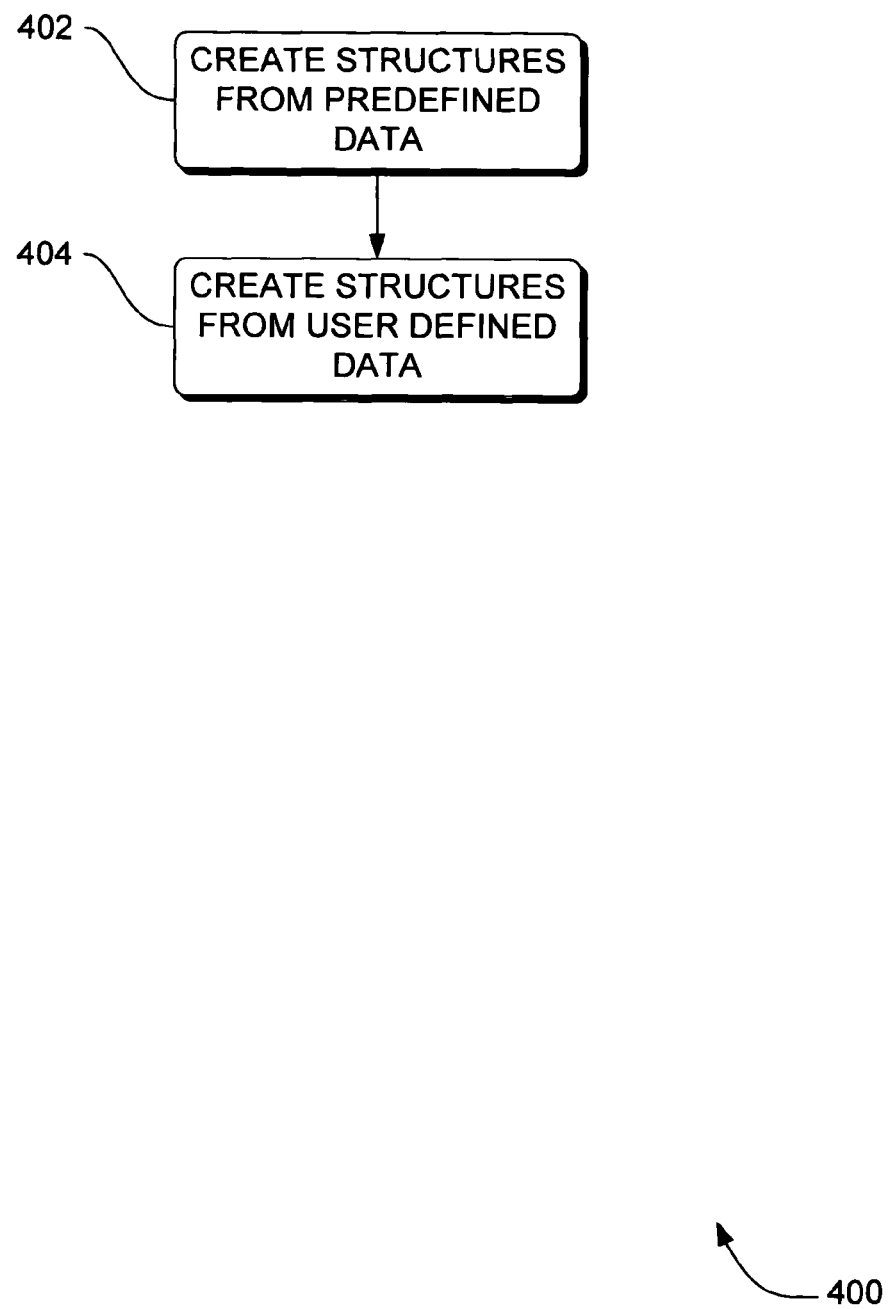
FIG. 4 is a flowchart of a method to manage groups of structures according to an embodiment.

FIG. 4 is a flowchart of a method 400 to manage groups of structures according to an embodiment. Method 400 solves the need in the art to reduce the challenge to humans in managing visual graphical objects. Method 400 also reduces time and improves precision of human clinicians in segmenting anatomical regions.

Method 400 includes creating 402 a plurality of structures from predefined data and creating 404 a structure from user-defined data. In method 400, predefined structures and structure groups (e.g. organs such as eye, lung, spleen, kidney, liver, abdomen, spinal cord, pelvis, etc.) are provided in the creating 402, but a user has the ability to create new structures or structure groups in the creating 404. That is, the capability to define structure (or structure group and add any structure to it) is provided to the user, either using an automatic process or manual drawing. In some embodiments, the manual drawing was created manually by a human user of a graphical software tool on a computer.

Each segmentation algorithm creates a structure group and separates the structures. In one example relating to the lung, segmentation creates a lung group and under the lung group is create two sub-structures: left-lung and right-lung. In another example of the eye, for three seed points (1-1 point in each eye ball and a $3_{rd}$ point at the meeting of optic nerves), seven structures are created (left and right eye balls, left and right lenses, left and right optic nerves, and chiasma), all belonging to the organs of sight. This requires the structure properties (e.g. name, color, type) to be defined previously. Accordingly, default structure properties are provided for and referenced by each process.

In some embodiments, these properties are changeable through a user interface. Thus, method 400 minimizes user interaction to start the segmentation and provides a convenient way of classifying related structures.

In some embodiments, software-base drawing tools are placed on a fixed or on a floatable toolbar. Floatable drawing toolbar can be placed on a graphical user interface near a drawing/viewing area. In a fixed toolbar that contains all of the functionalities, the user can drag a button out of the tool palette and drop the button onto a floating panel. The floating panel contains only those tools that the user dropped onto the floating panel, while all the functionalities are available at their original place. In case of computer systems having dual monitor support, this floatable toolbar is moveable to the second screen as well. In some embodiments of the toolbar, when the user changes the selected structure during drawing, then the previously used drawing tool remains active. In the case of computer systems that are operable to support a plurality of monitors or display devices, the floatable toolbar is moveable to any one of the plurality of monitors or display devices as well.

A "Review Mode" of the drawing toolbar switches off drawing mode, whereupon, the user does not have permissions to edit the selected structure. The drawing toolbar contains a "Create Structure" tool. Invoking the "Create Structure" tool creates a new and empty structure that is the active structure. The drawing toolbar also contains "Select structure" tool, which selects a structure with which to work. When the user selects a new structure, the selection in the table shall change and the previous structure is saved.

Some embodiments also include a measurement toolbar for measurement tools such as measure distance, angle, surface or ruler, grid etc.

Some embodiments also support customizations or preference by the user. User has the possibility to set which toolbars shall be visible, e.g. by checkboxes. Some graphical controls such as instructions, preferences of an opened (activated) panel are be hideable, in which the user can hide those controls. In some embodiments, preferences include toolbar settings, manual drawing settings, automatic outlining, organ segmentation settings and measurement settings, level of precision versus computation time and/or structure properties. In some embodiments, the system loads the previously saved settings. The user can select among options where default values are stored as preferences with the possibility to return to pre-set values (e.g. child or adult case, adult being the default; or the level of image contrast or noise, where the ones related to usual acquisition are the default).

In some embodiments, methods 200-400 are implemented as a computer data signal embodied in a carrier wave, that represents a sequence of instructions which, when executed by a processor, such as processor 504 in FIG. 5, cause the processor to perform the respective method. In other embodiments, methods 200-400 are implemented as a computer-accessible medium having executable instructions capable of directing a processor, such as processor 504 in FIG. 5, to perform the respective method. In varying embodiments, the medium is a magnetic medium, an electronic medium, or an optical medium.

Hardware and Operating Environment

FIG. 5 is a block diagram of a hardware and operating environment 500 in which different embodiments can be practiced. The description of FIG. 5 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 502 includes a processor 504, commercially available from Intel, Motorola, Cyrix and others. Computer 502 also includes random-access memory (RAM) 506, read-only memory (ROM) 508, and one or more mass storage devices 510, and a system bus 512, that operatively couples various system components to the processing unit 504. The memory 506, 508, and mass storage devices, 510, are types of computer-accessible media. Mass storage devices 510 are more specifically types of nonvolatile computer-accessible media and can include one or more hard disk drives, floppy disk drives, optical disk drives, and tape cartridge drives. The processor 504 executes computer programs stored on the computer-accessible media.

Computer 502 can be communicatively connected to the Internet 514 via a communication device 516. Internet 514 connectivity is well known within the art. In one embodiment, a communication device 516 is a modem that responds to communication drivers to connect to the Internet via what is known in the art as a "dial-up connection." In another embodiment, a communication device 516 is an Ethernet® or similar hardware network card connected to a local-area network (LAN) that itself is connected to the Internet via what is known in the art as a "direct connection" (e.g., T1 line, etc.).

A user enters commands and information into the computer 502 through input devices such as a keyboard 518 or a pointing device 520. The keyboard 518 permits entry of textual information into computer 502, as known within the art, and embodiments are not limited to any particular type of keyboard. Pointing device 520 permits the control of the screen pointer provided by a graphical user interface (GUI) of operating systems such as versions of Microsoft Windows®. Embodiments are not limited to any particular pointing device 520. Such pointing devices include mice, touch pads, trackballs, remote controls, touchscreens, point sticks and other special input devices designed for a specific application. Other input devices (not shown) can include a microphone, joystick, game pad, satellite dish, scanner, or the like.

In some embodiments, computer 502 is operatively coupled to a display device 522. Display device 522 is connected to the system bus 512. Display device 522 permits the display of information, including computer, video and other information, for viewing by a user of the computer. Embodiments are not limited to any particular display device 522. Such display devices include cathode ray tube (CRT) displays (monitors), as well as flat panel displays such as liquid crystal displays (LCD's). In addition to a monitor, computers typically include other peripheral input/output devices such as printers (not shown). Speakers 524 and 526 provide audio output of signals. Speakers 524 and 526 are also connected to the system bus 512.

Computer 502 also includes an operating system (not shown) that is stored on the computer-accessible media RAM 506, ROM 508, and mass storage device 510, and is and executed by the processor 504. Examples of operating systems include Microsoft Windows®, Apple MacOS®, Linux®, UNIX®. Examples are not limited to any particular operating system, however, and the construction and use of such operating systems are well known within the art.

Embodiments of computer 502 are not limited to any type of computer 502. In varying embodiments, computer 502 comprises a PC-compatible computer, a MacOS®-compatible computer, a Linux®-compatible computer, or a UNIX®-compatible computer. The construction and operation of such computers are well known within the art.

Computer 502 can be operated using at least one operating system to provide a graphical user interface (GUI) including a user-controllable pointer. Computer 502 can have at least one web browser application program executing within at least one operating system, to permit users of computer 502 to access an intranet, extranet or Internet world-wide-web pages as addressed by Universal Resource Locator (URL) addresses. Examples of browser application programs include Netscape Navigator® and Microsoft Internet Explorer®.

The computer 502 can operate in a networked environment using logical connections to one or more remote computers, such as remote computer 528. These logical connections are achieved by a communication device coupled to, or a part of, the computer 502. Embodiments are not limited to a particular type of communications device. The remote computer 528 can be another computer, a server, a router, a network PC, a client, a peer device or other common network node. The logical connections depicted in FIG. 5 include a local-area network (LAN) 530 and a wide-area network (WAN) 532. Such networking environments are commonplace in offices, enterprise-wide computer networks, intranets, extranets and the Internet.

When used in a LAN-networking environment, the computer 502 and remote computer 528 are connected to the local network 530 through network interfaces or adapters 534, which is one type of communications device 516. Remote computer 528 also includes a network device 536. When used in a conventional WAN-networking environment, the computer 502 and remote computer 528 communicate with a WAN 532 through modems (not shown). The modem, which can be internal or external, is connected to the system bus 512. In a networked environment, program modules depicted relative to the computer 502, or portions thereof, can be stored in the remote computer 528.

Computer 502 also includes power supply 538. Each power supply can be a battery.

Apparatus

Referring to FIGS. 6-12, a particular implementations are described in conjunction with the system overview in FIG. 1 and the methods described in conjunction with FIGS. 2-4.

Some embodiments of the structures of system 100 and methods 200-400 are organized in a tree structure in accordance with the occurrence of the structures in anatomy.

Figure 6:
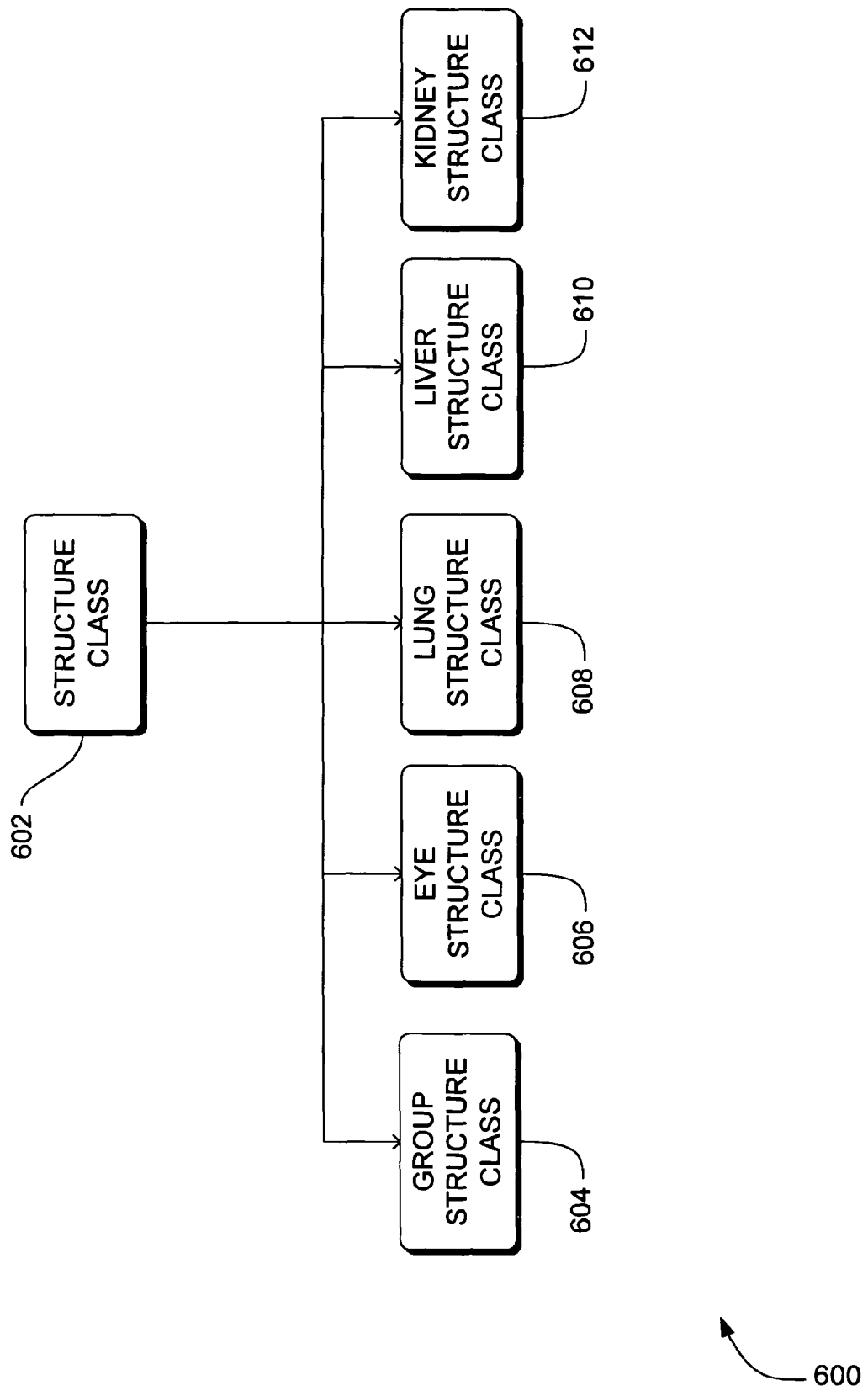
FIG. 6 is a block diagram of an hierarchical structure for use in an implementation.

FIG. 6 is a block diagram of an hierarchical anatomical object structure 600 for use in an implementation. FIG. 6 uses the Unified Modeling Language (UML), which is the industry-standard language to specify, visualize, construct, and document the object-oriented artifacts of software systems. In the figure, a hollow arrow between classes indicates that a child class below a parent class inherits attributes and methods from the parent class.

The hierarchical anatomical object structure 600 includes a structure class 602 that defines attributes (data) and methods (functions) of objects that are instantiated from the hierarchical anatomical object structure 600. At least four different child classes depend from the structure class 602 and inherit the attributes and methods of the structure class 602; a group structure class 604, an eye structure class 606, a lung structure class 608, a liver structure class 610, and a kidney structure class 612.

The group structure class 604 defines a structure class of a group of structures. The eye structure class 606 defines a structure class having attributes and functions that represent unique aspects of eye anatomy. The lung structure class 608 defines a structure class having attributes and functions that represent unique aspects of lung anatomy. The liver structure class 610 defines a structure class having attributes and functions that represent unique aspects of liver anatomy. The kidney structure class 612 defines a structure class having attributes and functions that represent unique aspects of kidney anatomy.

If user selects an organ-specific segmentation algorithm when no structure (or group) selected in the structure table, then there will be a new structure added to the table, if the result of the algorithm is only 1 structure; otherwise, the generated structures will belong to a newly generated structure group; all based on the predefined settings.

Figure 7:
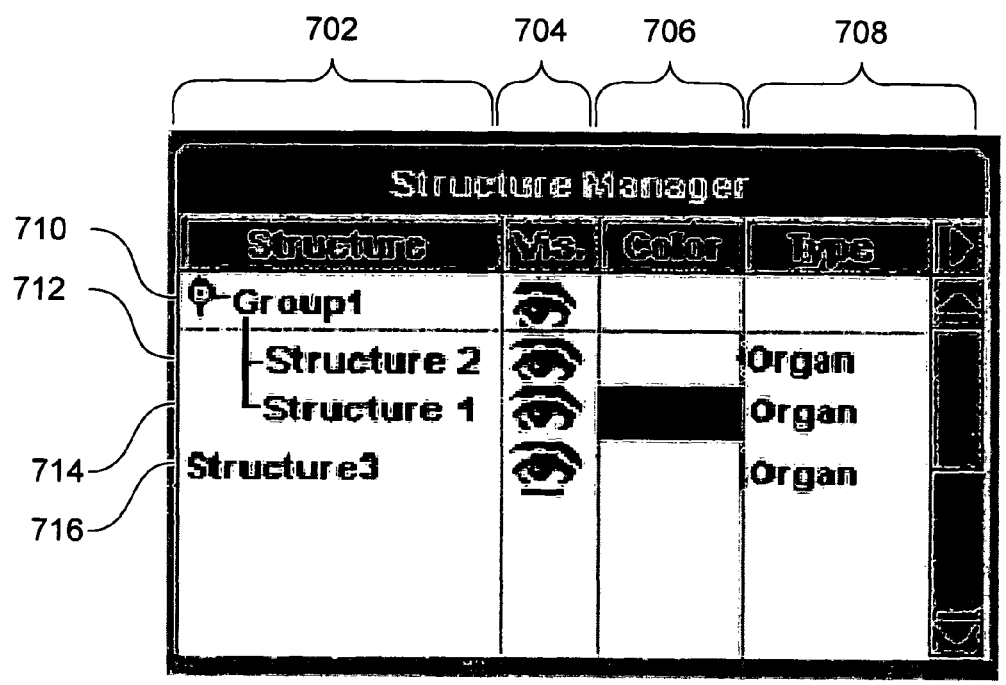
FIG. 7 is a graphical display of the relationship of a number of anatomical regions.

FIG. 7 is a graphical display 700 of the relationship of a number of anatomical regions. Graphical display 700 is display of the organized structures 110 in FIG. 1 created in accordance with the hierarchical anatomical object structure 600 in FIG. 6 by methods 200 in FIG. 2, 300 in FIG. 3 and/or method 400 in FIG. 4 in accordance with graphical user interfaces 800, 900, 1000 and 1100 below.

Graphical display 700 includes column or fields that indicate a structure name 702, visibility 704, color 706 and structure type 708 of at least one structure. In the example of graphical display 700, four structures are displayed. The first structure 710 shown in graphical display 700 is a group structure named "Group 1" that has visibility set, no color set, and no structure type.

The second structure 712 shown in graphical display 700 is a child structure of the "Group 1" 710 named "Structure 2" that has visibility set, color set to yellow, and an organ structure type. The third structure 714 shown in graphical display 700 is a child structure of the "Group 1" 710 named "Structure 1" that has visibility set, color set to blue, and an organ structure type. The fourth structure 716 shown in graphical display 700 is a structure not associated with any other structure that is named "Structure3" that has visibility set, color set to yellow, and an organ structure type.

In some embodiments, the child and parent structures 710, 712 and 714 are associated via links as discussed below FIG. 12. The structures can be linked in any one of a number of conventional link techniques, such as singly linked, doubly linked, recursively linked, and/or circularly linked lists.

In some embodiments, structures (e.g. instantiated objects of the classes in the hierarchical anatomical object structure 600) can be manipulated in a variety of ways through GUI 700. Parameters (e.g. name, visibility, color, type) of any structure or structure group that can modified. A table of the structures can be sorted based on the parameters and displayed. New structures can be added to an existing structure group. Existing structures can be deleted from a structure group. Empty structure groups can be created and structures added to it later. Structures can be dragged and dropped between structure groups on a graphical user interface. Graphical displays of structure groups can be opened or closed upon direction from user. An empty structure can be selected and named from a predefined list of names or named from a free-form text format. Multiple structures or structure groups can be selected. Structure contours can be changed with the drawing tools for all structures in selected group or outside a structure group. Union/join, difference, intersect and/or delete operations can be performed on a volume of structures or structure groups. When a user selects a segmentation algorithm and a structure group, then the generated structure(s) are associated with the selected structure group and a predefined structure group is added. When a user re-generates the structure group (re-run of a segmentation algorithm within the same structure group), then the previously deleted structures are generated again. When a user executes a segmentation algorithm that already executed, then the created structure names will differ. For example, adding a number to the end of the name. e.g.: lung segmentation, left_lung1 and right_lung1. Differentiator characters can be overwritten or appended at the end of groups and structures.

Figure 8:
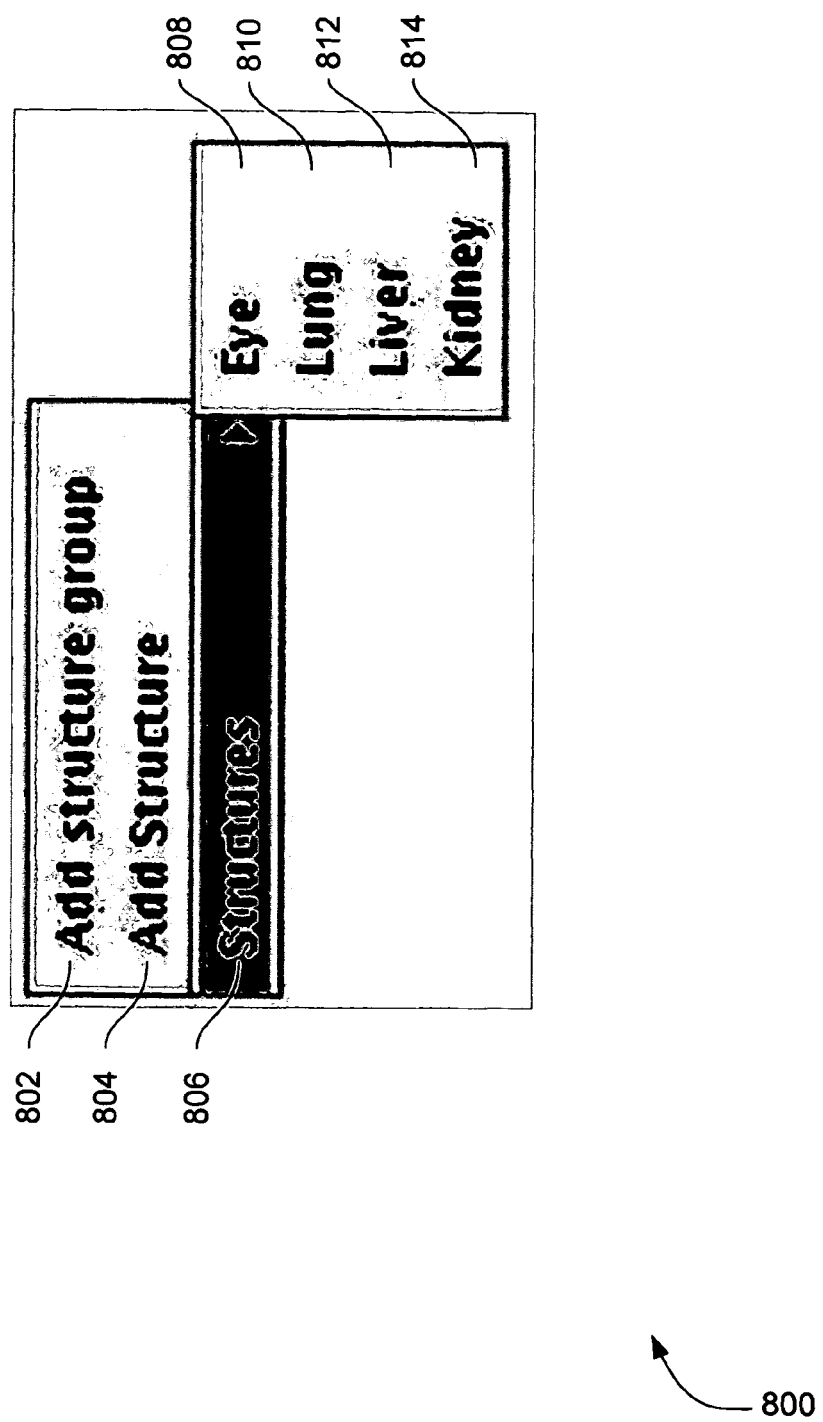
FIG. 8 is a graphical user interface that illustrates adding a structure on the hierarchical structure tree.

FIG. 8 is a graphical user interface (GUI) 800 reflecting the tree structure of the hierarchical anatomical object structure 600 in FIG. 6 that illustrates adding a structure.

At the highest menu level of GUI 800, three options are presented to the user; "add structure group" 802, "add structure" 804, and "structures" 806. Selecting "add structure group" 802 invokes instantiation of an object of the group structure class 604 of FIG. 6. Selecting "add structure" 804 invokes instantiation of an object of the structure class 602 of FIG. 6.

Selecting "structures" 806 invokes display of a second level menu of GUI 800, which presents four options to the user, "eye" 808, "lung" 810, "liver" 812 and "kidney" 814. Selecting "eye" 808 invokes instantiation of an object of the eye structure class 606 in FIG. 6. Selecting "lung" 810 invokes instantiation of an object of the lung structure class 608 in FIG. 6. Selecting "liver" 812 invokes instantiation of an object of the liver structure class 610 in FIG. 6. Selecting "kidney" 814 invokes instantiation of an object of the kidney structure class 612 in FIG. 6.

Figure 9:
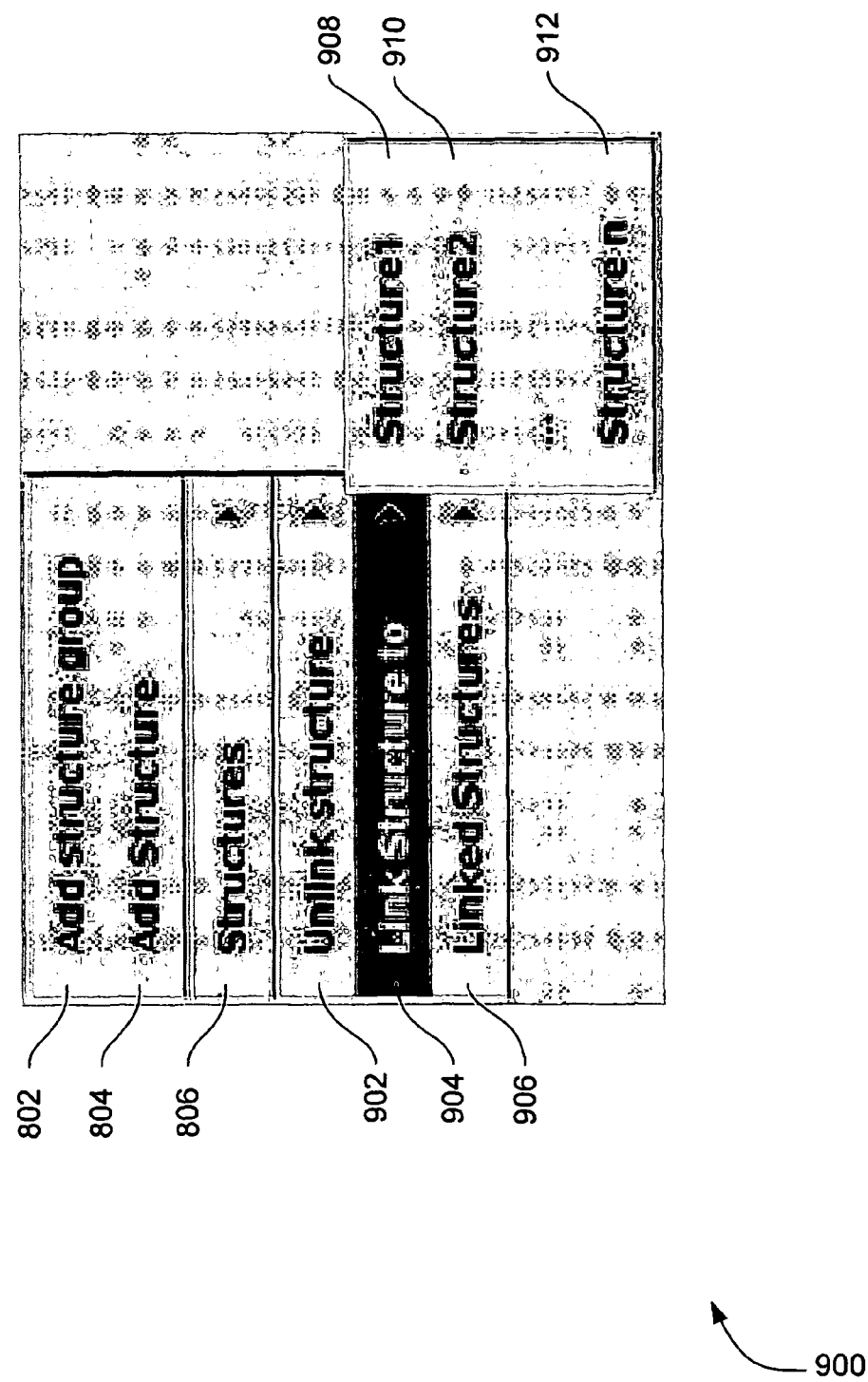
FIG. 9 is a graphical user interface that illustrates linking a structure on the hierarchical structure tree.

FIG. 9 is a graphical user interface (GUI) 900 reflecting the tree structure of the hierarchical anatomical object structure 600 in FIG. 6 that illustrates linking a structure.

At the highest menu level of GUI 900, at least three options are presented to the user; "unlink structure" 902, "link structure to" 904, and "linked structures" 906. Selecting "link structure to" 904 invokes display of a second level menu of GUI 900, which presents a list of the existing structures to which a structure can be linked. The example of GUI 900 displays a list of two structures, "structure1" 908, "structure2" 910 with other structures such as "structure n" 912.

Selecting "structure1" 908 invokes linking of a structure to the "structure1" structure. Selecting "structure2" 910 invokes linking of a structure to the "structure2" structure.

Figure 10:
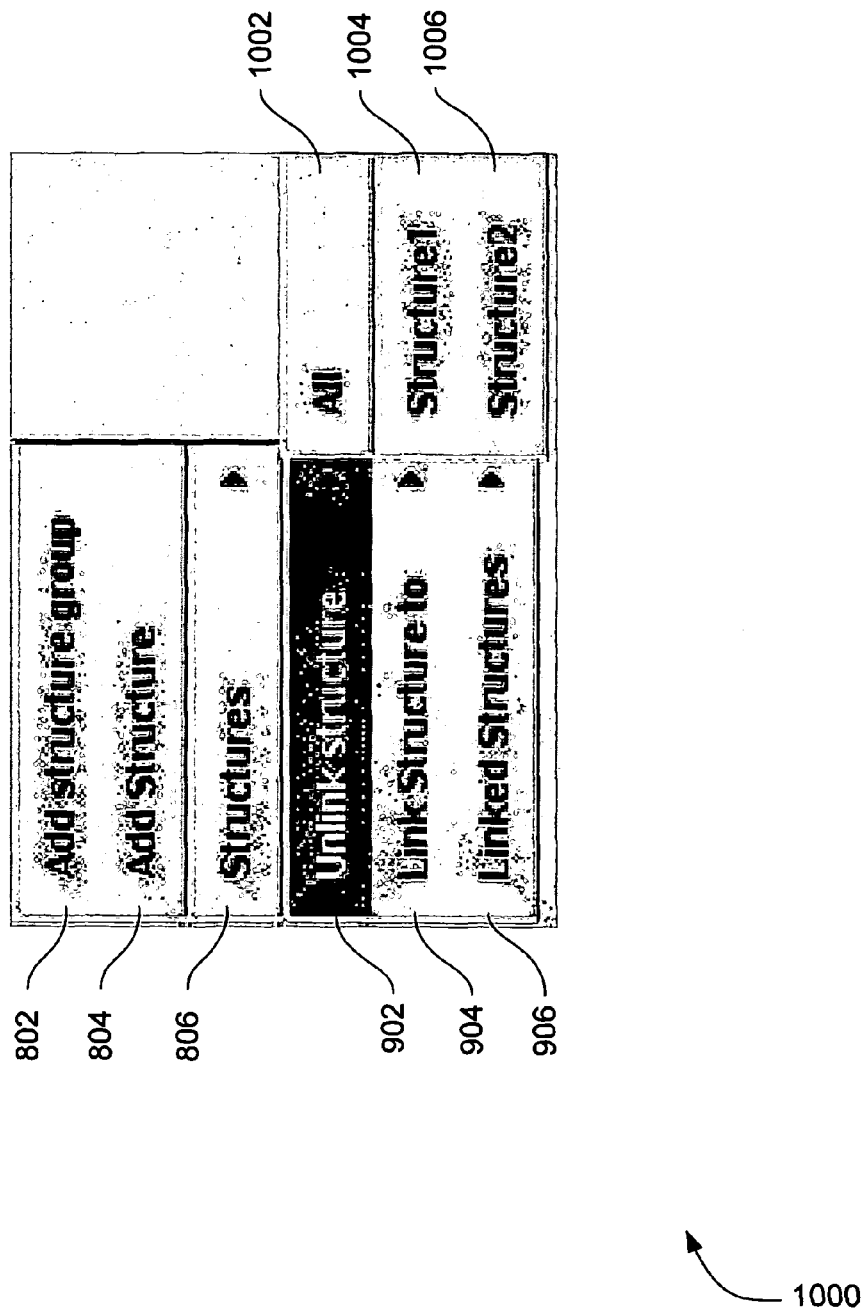
FIG. 10 is a graphical user interface that illustrates unlinking a structure on the hierarchical structure tree.

FIG. 10 is a graphical user interface (GUI) 1000 reflecting the tree structure of the hierarchical anatomical object structure 600 in FIG. 6 that illustrates unlinking a structure.

At the highest menu level of GUI 1000, at least three options are presented to the user; "unlink structure" 902, "link structure to" 904, and "linked structures" 906. Selecting "unlink structure" 902 invokes display of a second level menu of GUI 1000, which presents a list of the existing structures that can be unlinked. The example of GUI 1000 displays a list of three structures, ALL 1002, "structure1" 1004 and "structure2" 1006.

Selecting ALL 1002 invokes unlinking of all structures. Selecting "structure1" 1004 invokes unlinking of the "structure1" structure. Selecting "structure2" 1006 invokes unlinking of a structure to the "structure2" structure.

Figure 11:
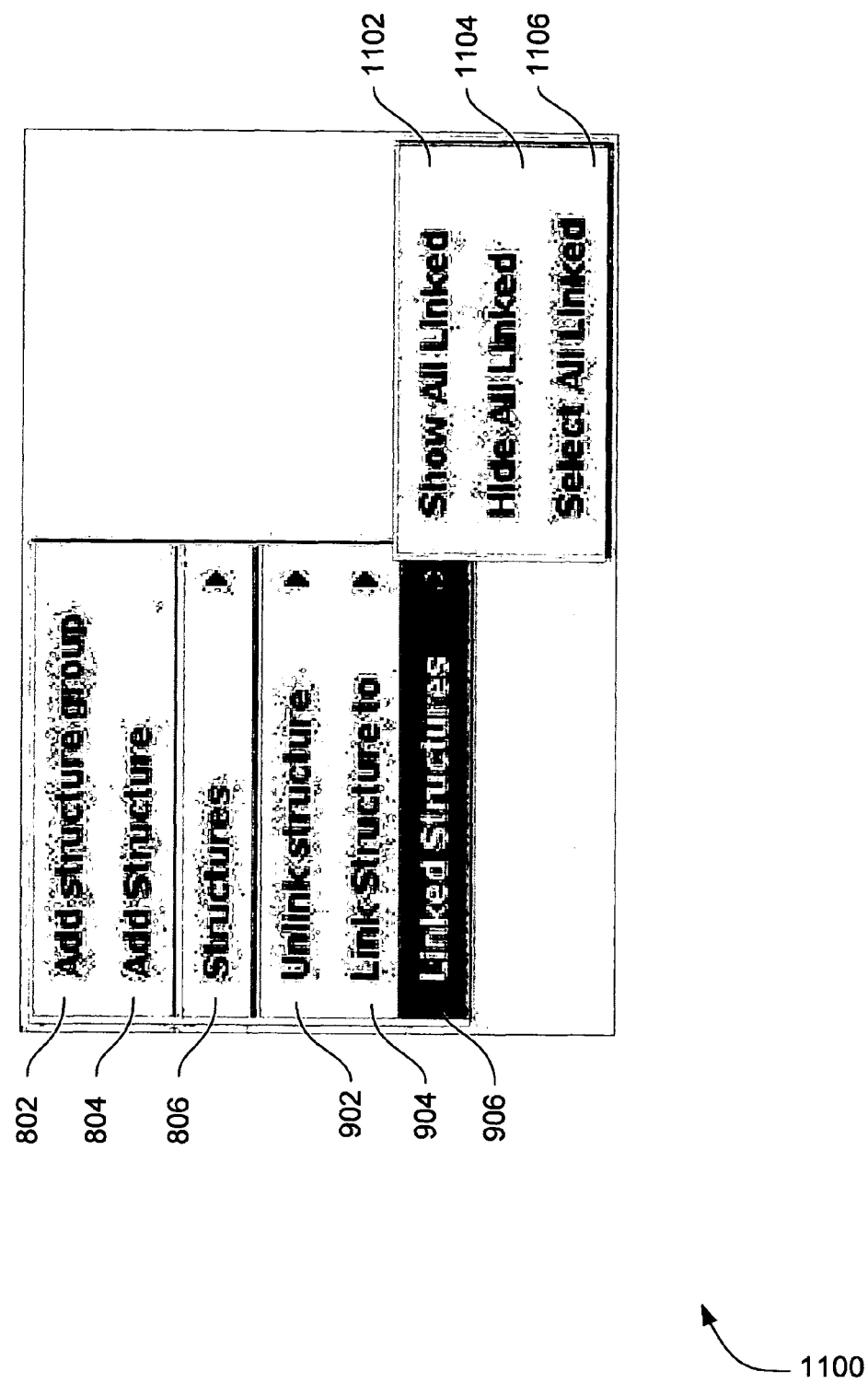
FIG. 11 is a graphical user interface that illustrates a variety of structure link functions on the hierarchical structure tree.

FIG. 11 is a graphical user interface (GUI) 1100 reflecting the tree structure of the hierarchical anatomical object structure 600 in FIG. 6 that illustrates a variety of structure link functions.

At the highest menu level of GUI 1100, at least three options are presented to the user; "unlink structure" 902, "link structure to" 904, and "linked structures" 906. Selecting "linked structure" 906 invokes display of a second level menu of GUI 1100, which presents a list of the structure functions. The example of GUI 1100 displays a list of three functions, "show all linked" 1102, "hide all linked" 1104 and "select all linked" 1106.

Selecting "show all linked" 1102 invokes display of all linked structures. Selecting "hide all linked" 1104 invokes non-display of all linked structures. Selecting "select all linked" 1106 invokes selecting all linked structures.

Figure 12:
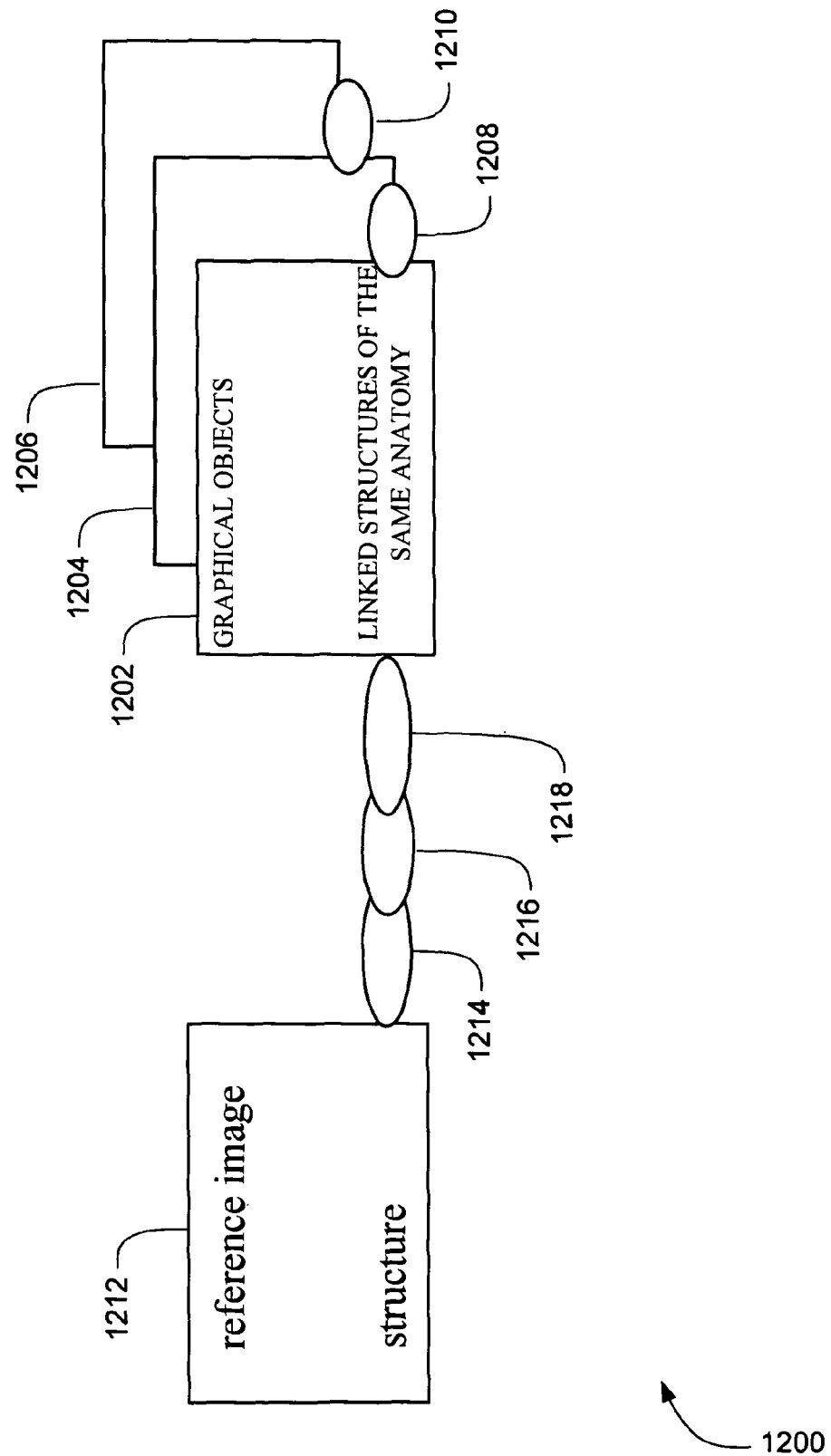
FIG. 12 is a block diagram that illustrates linked structures on the hierarchical structure tree.

FIG. 12 is a block diagram of structure architecture 1200 of tree structure of the hierarchical anatomical object structure 600 in FIG. 6 that illustrates linked structures. Structure architecture 1200 shows related manifests of an anatomical part on different images linked together, showing an embodiment in which the different graphical objects have been created and stored, while tracking changes between different modalities or between different phases.

In structure architecture 1200, a group of graphical objects (and their container structures) 1202, 1204 and 1206 that are related manifests of the same (group of) anatomical region(s) or organ(s) at different modalities or phases have linked status through links 1208 and 1210 to each other and to a reference image series 1212 through links 1214, 1216 and 1218.

In some embodiments, the linked status is created upon instantiation of the structures. In some embodiments, structures and/or a group of structures are manually linked or unlinked at the direction of the user as shown in GUI 900 and GUI 1000 above.

Thus, structure architecture 1200 supports easy follow-up of structures or group of structures through multiple modalities and phases by providing the "linked" status in a flexible way.

Structure architecture 1200 is operable for multi-modality and/or multi-phase structure handling. In some embodiments, multi-modality is supported as follows: One image series has a unique role, it is called "reference modality image series" such as reference image series 1212. An image series having any kind of modality can be selected as reference image series 1212. A user contours (both manually and automatically) anatomical regions 1202, 1204 and 1206 on a reference image 1212, such as a CT image. The contours are automatically transferred to other fused images (e.g. MR or PET images). During automatic transformation, the effect of difference in resolution between modalities (e.g. CT v.s. PET) is automatically corrected.

The automatically transferred structures will be created in the same structure group as the reference structure belongs to (if any). The user can inhibit automatic transfer. For example, the user contours and visualizes specifically pelvic bones on CT only, and bladder on MR only. Optionally, the user draws the contours of the same anatomical region or organ on any other image, independently of the contours drawn on the reference image. Meanwhile, changing between modalities is allowed. The user can modify the automatically transferred contours, which does not affect the linked status.

When the user directs modification of the contours on the reference image 1212, the corresponding contours are optionally aligned on the other (fused) images 1202, 1204 and 1206. The transferred structure or structure group name will differ (e.g. add a reference to modality to the end of the name. e.g.: left_lung_CT and right_lung_CT as well left_lung_PET and right_lung_PET).

The user optionally names the structure or structure group of the same anatomical region or organ, drawn independently on the different modalities, in a way reflecting their relationship (e.g. left_lung_CT and and left_lung_PET). After that these structures have linked status. Optionally, a differentiator character is overwritten or appended at the end, for groups and structures as well. This will not affect the linked status.

During a "Modality Review Mode," all selected structures such as 1202, 1204 and 1206 that are linked to the reference image 1212 are displayed, regardless on which image the graphical object contours were created. In addition, contours and the contained regions of the graphical object can be shown in review mode.

In some embodiments, color codes are displayed to indicate how much percentage of regions is common. As an example, red would indicate common regions for most of the contours, orange, yellow, green decreasing common regions, while blue would indicate region only part of one structure.

The operations of union/join, difference and intersection on the volume of selected structures or structure groups are also performed at the direction of the user. The resulting graphical object of the reference image is displayed. In one example, this is useful in comparing differences in a bladder CT or MR image. Another option is to apply any of the previously listed operations to linked structures only.

Common operations (e.g.: show/hide contour, select all) can also be performed on the linked structures. A user can direct unlinking of only one structure from a linked group of structures. A user can direct unlinking (i.e. breaking) all connections in the linked group of structures. The user can also direct linking a new structure to the reference structure later.

In some embodiments, multi-phase is supported as follows: One image series is a "reference phase image series" such as reference image series 1212. An image series having any order number of phase in a temporal sequence can be selected as reference image series.

A user contours graphical objects (both manually and automatically) on a reference phase (e.g. phase when contrast just injected). The contours are transferred to the other image phases. During the automatic transformation, misplacement between phases (e.g. due to breathing) is corrected. The transferred structures are created in the same structure group that the reference structure belongs to (if any).

The user can direct inhibition of the transfer. For example, the user directs contouring and display of a specific phase only. Optionally, user draws the contours of the same object or organ on any phase, independently of the contours drawn on the reference phase. Meanwhile, changing between phases is allowed. The user can also direct modification of the transferred contours. This modification has no effect on the linked status. When the user directs modification of the contours on the reference phase, the system aligns the corresponding contours on the other phases, as directed by the user. The transferred structure or structure group name will differ (e.g. add a reference to phase to the end of the name. e.g.: left_lung_ph10 and right_lung_ph10). The user can direct naming of the structure or structure group of the same object or organ, drawn independently on the different phases, in a way reflecting their relationship (e.g. left_lung ph10 and and left_lung_ph20). Thereafter, these structures will have a linked status. After that these structures have linked status. Optionally, a differentiator character is overwritten or appended at the end, for groups and structures as well. This will not affect the linked status.

An image is generated that has intensity values as Maximum Intensity Projections (MIP) of the selected phases. The user can select any combination of phases to be a basis of MIP phase.

During a "MIP Review Mode," all selected structures such as 1202, 1204 and 1206 that are linked to the reference image 1212 are displayed, regardless of which phase the structure contours were created. In addition, contours and the contained regions can be shown in review mode.

In some embodiments, color codes are displayed to indicate what percentage of regions is common. As an example, red would indicate common regions for most of the contours, orange, yellow, green decreasing common regions, while blue would indicate region only part of one structure.

The operations of union/join, difference and intersection on the volume of selected structures or structure groups are also performed at the direction of the user. The resulting graphical object of the reference image is displayed. In one example, this is useful in comparing differences in a bladder CT or MR image. Another option is to apply any of the previously listed operations to linked structures only.

Common operations (e.g.: show/hide contour, select all) can also be performed on the linked structures. A user can direct unlinking of only one structure from a linked group of structures. A user can direct unlinking (i.e. breaking) all connections in the linked group of structures. The user can also direct linking a new structure to the reference structure later.

The structure and contour handling system preferences are also extended with multi-modality settings (e.g. preferred reference image type) and multi-phase settings (e.g. preferred reference phase type).

In some embodiments of the contouring, various ways of manual drawing (tracing or point-to-point click) and editing can be performed by interactively modifying (correcting) manual outlines to attach to nearby visible borders i.e. gray value differences. In some embodiments, interpolation between contours, regardless if the contours are drawn on the same type of slices (e.g. only on axial slices) or any mix of slices (e.g. axial/sagittal/coronal slices). In some embodiments, contours are copied from a previous slice or a template is provided either in 2D or 3D forms such circle, ellipse, rectangle, sphere, ellipsoid, etc. An outline is created by either thresholding or implementing morphological operators (e.g. remove bridges, fill holes, largest components, margins).

Apparatus components can be embodied as computer hardware circuitry or as a computer-readable program, or a combination of both. In another embodiment, the system, apparatus and methods are implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 502 in FIG. 5, or on at least as many computers as there are components.

CONCLUSION

A management system of three dimensional graphical objects is described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in object-oriented terms, one of ordinary skill in the art will appreciate that implementations can be made in a procedural design environment or any other design environment that provides the required relationships.

The systems, method and apparatus described above is a complex system, yet is an efficient and user-friendly system, which manages organization of structures, graphical objects and manual/automated contouring (segmentation). The systems, method and apparatus described above are suitable for any kind of image modality and any kind of segmentation algorithm.

This system eases organization of graphical objects and structures by flexible usage of structure groups. That is, the system creates, stores, retrieves and combine anatomically relevant parts.

The systems, method and apparatus described above is applicable to structure handling from explicit or implicit creation of visual graphical object of anatomical regions, via drawing the contour of the anatomical region either manually (tracing, follow up) or automatically (thresholding, organ segmentation), to structure management and usage. A segmentation workflow can be used in two different ways. The first way highly supports user interaction, intended for organs that are difficult to segment fully automatically (e.g. because of low contrast). Another process supports batch mode, intended for organs whose segmentation is relatively long.

The systems, method and apparatus described above provide easy-to-use workflow in the correct order. The systems, method and apparatus described above elevates abstraction level, provides consistent organization with clean layout, while allowing a user to maintain control during the segmentation process with a large number of choices and options.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application is meant to include all object-oriented, database and communication environments and alternate technologies which provide the same functionality as described herein.

The invention claimed is:

1. A non-transitory computer-accessible medium having executable instructions to manage structure architecture comprising:
   a workflow system operable to receive a plurality of medical images and at least one user input from an external source;
   a plurality of structures on a reference image, each structure being a related manifest of the same anatomical region or organ at different modalities or phases;
   a linked status to each structure; and
   at least one link between the first structure on the reference image and the structure on the second image relating to the same anatomical region or organ as the first structure relates, wherein the structure architecture is operable for multi-modality and multi-phase structure handling, and wherein the multi-modality is supported in which one image has a unique role as the reference image, an image having any kind of modality can be selected as the reference image, a user contours anatomical regions on the reference image and the contours are transferred to other fused images.

2. The structure architecture of claim 1, wherein the structure architecture supports easy follow-up of structures or groups of structures through multiple modalities and multiple phases by providing a linked status.

3. The structure architecture of claim 1, wherein the multi-phase is supported in which one image has a unique role as a reference phase image, an image having any kind of phase can be selected as reference image, a user contours anatomical regions on a reference image and the contours are transferred to other fused images.

4. A non-transitory computer-accessible medium having executable instructions to manage structure group architecture comprising:
   a workflow system operable to receive a plurality of medical images and at least one user input from an external source;
   a plurality of structure groups on a reference image, each structure group being a related manifest of the same set of anatomical regions or organs at different modalities or phases;
   a linked status to each structure group; and
   at least one link between the first structure group on the reference image and the structure group on the second image relating to the same anatomical region or organ as the first structure group relates, wherein the structure group architecture is operable for multi-modality structure handling, and wherein the multi-modality is supported in which one image has a unique role as the reference image, an image having any kind of modality can be selected as the reference image, a user contours anatomical regions on the reference image and the contours are transferred to other fused images.

* * * * *